United States Patent [19]
Kelman

[11] Patent Number: 4,586,930
[45] Date of Patent: May 6, 1986

[54] INTRAOCULAR LENS AND METHOD OF PREPARING THE SAME FOR INSERTION INTO A HUMAN EYE

[76] Inventor: Charles D. Kelman, North Shore Towers, 269 Grand Central Parkway, Floral Park, N.Y. 11005

[21] Appl. No.: 481,782

[22] Filed: Apr. 4, 1983

[51] Int. Cl.$^4$ ................................................ A61F 2/16
[52] U.S. Cl. ........................................ 623/6; 206/5.1; 206/438; 206/570
[58] Field of Search .................. 3/13, 1; 206/5.1, 210, 206/438, 570

[56] References Cited

U.S. PATENT DOCUMENTS

| | | | |
|---|---|---|---|
| 4,113,088 | 9/1978 | Binkhorst | 3/13 X |
| 4,118,808 | 10/1978 | Poler | 3/13 |
| 4,122,556 | 10/1978 | Poler | 3/13 |
| 4,134,160 | 1/1979 | Bayers | 3/13 |
| 4,159,546 | 7/1979 | Shearing | 3/13 |
| 4,249,271 | 2/1981 | Poler | 3/13 |
| 4,280,232 | 7/1981 | Hummel | 3/13 |
| 4,298,995 | 11/1981 | Poler | 3/13 |

OTHER PUBLICATIONS

American Medical Optics, Model PC-80, Posterior Chamber, (Knolle), Intraocular Lenses, American Hospital Supply Corp., 1402 East Alton Ave., Irvine, CA 92714 (advertisement), 4 pages, Sep. 1982.
Lens Styles from Cilco, advertisement brochure, Cilco, Inc., 1616 13th Ave., Box 1680, Huntington, WV 25717, pp. 1, 2 and 6, Oct. 1982.

*Primary Examiner*—Ronald L. Frinks
*Attorney, Agent, or Firm*—Henry Sternberg; Bert J. Lewen

[57] ABSTRACT

A posterior chamber intraocular lens having position-fixation legs extending from the lens body and having a suture loosely engaging one of the legs and extending through an aperture in the lens body. Prior to insertion of the lens into a human eye, the surgeon tightens the suture to deform said position-fixation leg to a position adjacent the lens body to facilitate passing that position-fixation leg through the pupil and by the iris for seating in the cul-de-sac between the anterior and posterior capsules after the other position-fixation leg is seated in such cul-de-sac.

11 Claims, 4 Drawing Figures

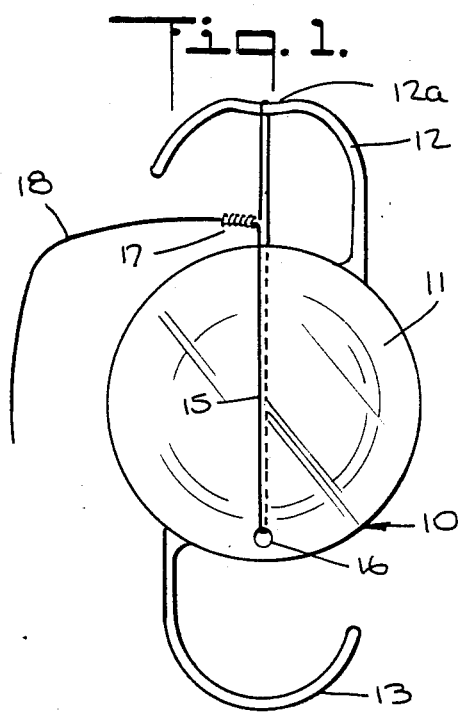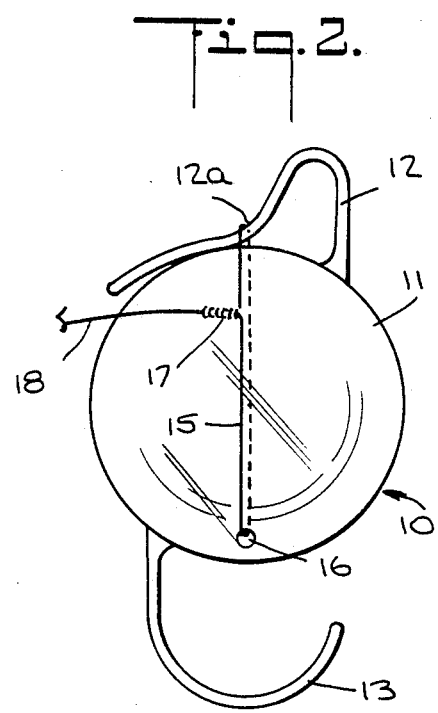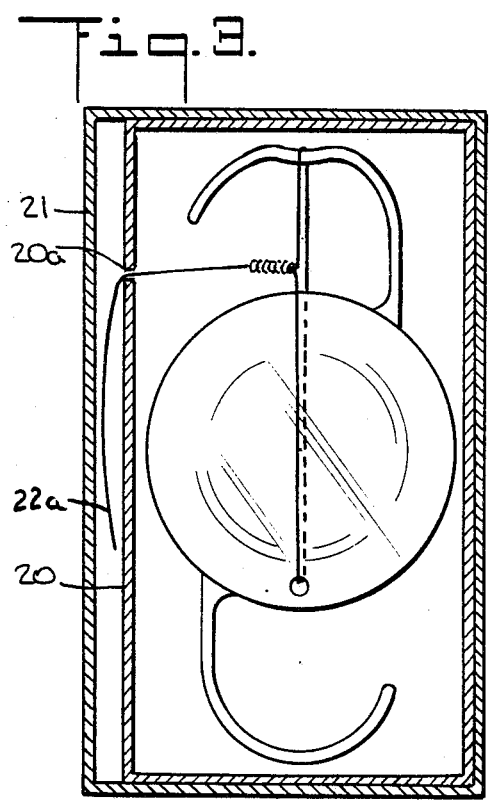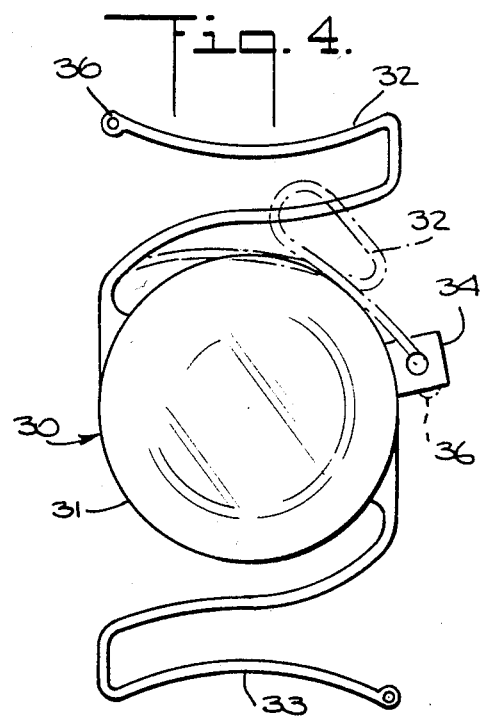

INTRAOCULAR LENS AND METHOD OF PREPARING THE SAME FOR INSERTION INTO A HUMAN EYE

This invention relates to intraocular lenses and, more particularly, to intraocular lenses suitable for use as posterior chamber lenses. The invention also relates to methods of preparing intraocular lenses for insertion into human eyes.

Heretofore, posterior chamber lenses which have been seated in the cul-de-sac between the anterior and posterior capsules have generally required flexing of one of the position-fixation means of the lens by the surgeon after the lower position-fixation means of such lens has been seated in the sul-de-sac between the anterior and posterior capsules in order to reduce the size of the lens so as to facilitate passing the upper position-fixation means through the pupil and past the iris and to seat the upper position-fixation means in the above mentioned cul-de-sac. This is a delicate and complex procedure. When it is necessary to push down on the upper position-fixation means in order to be able to move the latter through the pupil, the pressure thus exerted is transmitted to the tissues of the cul-de-sac seating the lower position-fixation means. This pressure is often enough to rupture the zonules in the region of the cul-de-sac with the result that the implanted lens sinks (known as the "setting sun syndrome") to a position in which its optic is no longer in optical alignment with the eye.

It is an object of the present invention, therefore, to provide a new and improved intraocular lens which avoids one or more of the above-mentioned disadvantages and limitations of prior such lenses.

It is another object of this invention to provide a new and improved intraocular lens which avoids the necessity for the surgeon to bend one of the position-fixation means of a posterior chamber lens after the lower position-fixation means has been seated in the eye.

It is another object of the invention to provide a new and improved method of preparing an intraocular lens for insertion into a human aye which avoids one or more of the disadvantages and limitations of prior such methods.

It is another object of this invention to provide a new and improved method of preparing an intraocular lens for insertion into a human eye which avoids the necessity for the surgeon to bend one of the position-fixation means of the lens after the lens has been inserted into the eye.

In accordance with the invention, an intraocular lens comprises a light-focusing lens body and flexible position-fixation means joined to the lens body for positioning the lens body in the interior of a human eye. The position-fixation means has at least one portion adapted to be loosely connected to a portion of the lens body. The lens also includes means for loosely connecting the aforesaid at least one portion of the position-fixation means to the aforesaid portion of the lens body. The connecting means is adapted to be tightened by a surgeon prior to insertion of the lens in an eye to flex the position-fixation means so as to move the aforesaid at least one portion of the position-fixation means towards the aforesaid portion of the lens body.

Also in accordance with the invention, an intraocular lens comprises a light-focusing lens body and a pair of flexible position-fixation means joined to the lens body for positioning the lens body in the interior of a human eye. One of the position-fixation means has at least one portion which is adapted to be loosely connected to a portion of the lens body by a surgeon prior to insertion of the lens in an eye. The lens also includes means for loosely connecting only the aforesaid one of the position-fixation means to the aforesaid portion of the lens body.

Also in accordance with the invention, a method of preparing an intraocular lens having a lens body and flexible position-fixation means joined thereto for insertion into a human eye through an opening therein comprises applying means for loosely connecting at least one portion of the position-fixation means to a portion of the lens body. The method also includes tightening the connecting means prior to insertion of the lens into an eye to bend the aforesaid at least one portion of the position-fixation means towards the aforesaid portion of the lens body.

Also in accordance with the invention, a method of preparing an intraocular lens having a lens body and flexible position-fixation means joined thereto for insertion into a human eye through an opening therein comprises temporarily connecting the position-fixation means to a portion of the lens body prior to insertion of the lens into an eye temporarily to deform the position fixation means.

Also in accordance with the invention, a method of preparing an intraocular lens having a lens body and flexible position-fixation means joined thereto for insertion into a human eye through an opening therein comprises applying a substance which is compatible with the eye and soluble in the eye to the position-fixation means and to another portion of the lens prior to insertion of the lens into an eye temporarily to adhere the position fixation means to the aforesaid other portion of the lens.

For a better understanding of the present invention, together with other and further objects thereof, reference is made to the following description taken in connection with the accompanying drawings, and its scope will be pointed out in the appended claims.

Referring now to the drawings:

FIG. 1 is a plan view of an intraocular lens constructed in accordance with the invetion;

FIG. 2 is a plan view of the FIG. 1 lens in another condition prior to insertion into a human eye;

FIG. 3 is a plan view of a lens constructed in accordance with the invention inside a container with an upper portion of the container removed to show the lens clearly; and FIG. 4 is a plan view of another lens constructed in accordance with the invention with one of the position-fixation means in a deformed condition represented in broken-line construction.

Referring now more particularly to FIG. 1 of the drawings, there is represented an intraocular lens 10 comprising a light-focusing lens body 11 and flexible position-fixation means 12, 13 joined to the lens body 10 for positioning the lens body in the interior of a human eye. The lens body 11 may be constructed of any biologically inert and transparent material suitable for optical correction such as polymethylmethacrylate, quartz, opthalmic glass and other materials known in the art.

The position-fixation means 12, 13 may also be, for example, of polymethylmethacrylate and may be molded integrally with the lens body 11 or connected by ultrasonic welding, fusion, or any other connection method known in the art. The position-fixation means 12, 13 are resilient or springy such that they will each return to an undeformed condition after deformation from the undeformed configuration. For example, the undeformed configuration of the position-fixation means 13 is represented in FIG. 1 while the position-fixation means 12 has a slight deformation at portion 12a. The lens can be of any suitable type for use in the posterior chamber and the lens body 11 and position-fixation members 12, 13 may, for example, be of the type utilized in a conventional Shearing lens.

The position-fixation means 12 has at least one portion 12a adapted to be loosely connected to a portion of the lens body 11. The lens 10 includes means for loosely connecting at least one portion 12a of the position-fixation means 12 to a portion of the lens body. The connecting means is adapted to be tightened by a surgeon prior to insertion of the lens in an eye to flex the position-fixation means 12 so as to move at least one portion 12a of the position-fixation means towards the aforesaid portion of the lens body. More particularly, the connecting means preferably comprises a suture 15 which passes through an aperture 16 near the outer edge of the lens body 11 and which forms a loop adapted to be tightened quickly, for example, in the configuration of a hangman's noose. The aforesaid one portion 12a of the position-fixation means and the aperture 16 of the lens body 11 preferably are located at different peripheral regions of the lens body 11 so that the suture 15 extends across the lens body 11.

Preferably, the suture 15 is applied around the position-fixation means 12 and through the aperture 16 by the manufacturer of the lens to loosely connect the position-fixation means 12 to the lens body 11 through the aperture 16. The aperture 16 is located preferably diametrically opposite the portion 12a with respect to the lens body 11. Prior to insertion of the lens 10 into an eye, the surgeon can quickly tighten the loop formed by the suture 15, by pulling portion 18 with respect to the wrapped portion 17, to bend the position-fixation means 12 to a position where the portion 12a is adjacent the lens body 11, as represented in FIG. 2. The suture 15 remains in a tightened position after the tightening force applied by the surgeon has been removed due to the friction of the wrapped portion 17 around the portion 18. The suture is preferably made of nylon.

Referring now more particularly to FIG. 3 of the drawings, a lens similar to the FIG. 1 lens is there represented as housed in a container 20 within an outer container 21. Container 20 has an opening 20a therein through which free end portion 22a of the connecting means or suture 22 passes. The connecting means 22, preferably a nylon suture, may be pulled by a surgeon to tighten the loop around the lens body and the position-fixation means after the container 21 is opened, but before the container 20 is opened. Everything inside container 21 is, of course, sterilized. Container 21 is required only to maintain the sterility of the lens and the suture 22 including the portion thereof which extends thru the opening 20a. After opening of container 20, the surgeon may remove lens 10 from the container with its loop in tightened condition. Removal of the lens results in drawing the end 22a of suture 22 back through the opening 20a.

Referring now particularly to FIG. 4, there is represented an intraocular lens 30 having a light-focusing lens body 31 and a pair of flexible position-fixation means 32, 33 joined to the lens body for positioning the lens body in the interior of a human eye. The lens body 30 and the position-fixation means 32, 33 may all be for example, of polymethylmethacrylate. A lens of this type, but without the means 34 to be described subsequently, is described and claimed in my co-pending application entitled Intraocular Lens, Ser. No. 465,573, filed Feb. 10, 1983. The position-fixation means 32 is adapted to be loosely connected to a portion 34 of the lens body 31 by a surgeon prior to insertion of the lens into an eye. The lens includes means 34 for loosely connecting only one of the position-fixation means 32, 33 to the portion 35 of the lens body. The means 34 may, for example, comprise a flange integral with the lens body 31 and having an opening therein through which the end 36 of the position-fixation means 32 may be placed by the surgeon prior to insertion of the lens in the eye, as represented in broken-line construction in FIG. 2. The end 36 of the position-fixation means 32 is sufficiently large that it will not slip back through the opening 32 prior to being pulled back therethrough by the surgeon. The lens may then be inserted into the eye and positioned in a manner similar to that previously discussed.

From the foregoing explanation with reference again to FIGS. 1 and 2 it will be apparent that a method of preparing an intraocular lens having a lens body 11 and flexible position-fixation means 12, 13 joined thereto for insertion into a human eye through an opening therein comprises applying means 15 for loosely connecting at least one portion 12a of the position-fixation means 12, 13 to a portion of the lens body and tightening the connecting means 15 preferably just prior to insertion of the lens into an eye to bend at least one portion 12a of the position-fixation means 12, 13 toward the aforesaid portion of the lens body. The method preferably also includes the step of maintaining the connecting means 15 in tightened condition during insertion of the lens into the eye and releasing the connecting means 15 from the tightened condition when seating the lens in the eye, for example, by the surgeon's cutting the suture 15. The method also preferably includes the step of seating another portion of the position-fixation means 13 in the posterior chamber of the eye, moving the one portion 12a of the position-fixation means 12 through the pupil also into the posterior chamber and thereafter releasing the connecting means 15 from its tightened condition into its loosened condition thereof. Preferably the step of releasing the connecting means 15 from the tightened condition when seating the lens 10 in the eye comprises releasing the connecting means 15 after seating a first portion of the position-fixation means 13 in the eye and prior to a second portion 12a of the position-fixation means 12 reaching its final position within the eye. Releasing the position-fixation means 12 preferably comprises cutting the suture 15 in the region thereof which overlies the central portion of lens body 11 and is therefore readily accessible to the surgeon thru the pupil.

Also in accordance with the invention, with reference again to FIG. 4, a method of preparing an intraocular lens 30 having a lens body 31 and a flexible position-fixation means 32, 33 joined thereto for insertion into a human eye through an opening therein comprises temporarily connecting the position-fixation means 32 to a portion 34 of the lens body prior to insertion of the lens into an eye temporarily to deform the position-fixation means 32. The step of temporarily connecting the position-fixation means to the portion 34 of the lens body 31 comprises temporarily connecting the position-fixation means 32 to the connecting means 34.

The method of preparing an intraocular lens for insertion into an eye may also comprise temporarily connecting the position-fixation means to another portion of the lens. The step of temporarily connecting the position-fixation means to another portion of the lens prior to insertion of the lens into an eye may comprise applying a substance, which is compatible with the eye and soluble in the eye, to the position-fixation means and to another portion of the lens prior to insertion of the lens into an eye temporarily to adhere the position-fixation means to the aforesaid other portion of the lens. More particularly, the method preferably comprises the step of applying a substance comprising liquid fibrin to the position-fixation means and to another portion of the lens, for example, the lens body, prior to the insertion of the lens into an eye and drying the fibrin prior to the insertion of the lens into an eye. For example, in FIG. 4 the means 34 could be eliminated and there could be applied a drop of fibrin connecting the end portion 36 with the portion 35.

After the lens has been inserted into the eye, the fibrin dissolves and the position-fixation means which has been temporarily deformed returns toward its undeformed condition for seating by the surgeon in the cul-de-sac between the anterior and posterior capsules of the eye.

From the foregoing description, it will be apparent that among the advantages achieved by this invention are (1) the speed and simplicity with which the surgeon can decrease the size of the lens prior to implantation; (2) the control the surgeon has over the amount of contraction of the position-fixation means of the lens; (3) the avoidance of decreased shelf life of the lens, since many lens materials would lose at least some of their resilience i.e. "memory" if they had to be packaged by the manufacturer in contracted condition; (4) avoiding injury to the eye tissue, which could result from having to bend one of the legs of the position-fixation means of the lens to pass it through the pupil after the other leg has already been seated in the posterior chamber; and (5) ease and simplicity of releasing the bent leg of the position-fixation means to return toward its original condition, due to the accessibility to the surgeon of a portion of the connecting means, after the lens is in the posterior chamber.

While there have been described what are at present considered to be the preferred embodiments of this invention, it will be obvious to those skilled in the art that various changes and modifications may be made therein without departing from the invention, and it is, therefore, aimed to cover all such changes and modifications as fall within the true spirit and scope of the invention.

What is claimed is:

1. An intraocular lens and container combination comprising:
    a lens having a light-focusing lens body and flexible position-fixation means joined to said lens body for positioning said lens body in the interior of a human eye, said position-fixation means having at least one portion adapted to be loosely connected to a portion of said lens body; and
    a container for protectively containing said lens prior to insertion of the lens in the eye, said container having an opening;
    means in said container for loosely connecting said at least one portion of said position-fixation means of said lens to said portion of said lens body, said connecting means having a portion thereof extending through said opening and being adapted to be tightened by a surgeon, from outside said container just prior to removal of said lens from said container for insertion of the lens in an eye, to flex said position-fixation means so as to move said at least one portion of said position-fixation means towards said portion of said lens body, said connecting means being adapted to remain in tightened condition after being tightened.

2. A lens and container combination in accordance with claim 1 in which said connecting means comprises a suture and one end of said suture extends through said opening.

3. A lens in accordance with claim 2 in which said suture has a wrapped portion and another portion which can slide through said wrapped portion in response to a tightening force.

4. A lens and container combination in accordance with claim 2 and a second container housing said first mentioned container, said second container having a space for containing said end of said suture extending through said opening.

5. A method of preparing an intraocular lens having a lens body and flexible position-fixation means joined thereto for insertion into a human eye through an opening therein comprising:
    applying suture means for loosely connecting at least one portion of said position-fixation means to a portion of said lens body;
    placing said lens in a first container having an opening;
    extending the free end of said suture means through said opening;
    placing said first container and said free end of said suture means in a second container for storage and/or shipment of the lens;
    tightening said suture means prior to insertion of the lens into an eye to bend said at least one portion of said position-fixation means towards said portion of said lens body.

6. A method in accordance with claim 5 further comprising removing said first container from said second container just prior to insertion of the lens in an eye; and said step of tightening comprising pulling the free end of said suture while said lens is still in said first container.

7. A method in accordance with claim 6 in which the step of applying said suture means comprises applying a suture having a wrapped portion and another portion which can slide through said wrapped portion in response to a tightening force.

8. A method in accordance with claim 7 in which said wrapped portion is effective to maintain said suture in a tightened condition after the tightening force is removed.

9. A method according to claim 6 further comprising maintaining said suture means in tightened condition during insertion of the lens into the eye and releasing said connecting means from said tightened condition when seating the lens in the eye.

10. A method according to claim 9 wherein said step of releasing said suture means from said tightened condition when seating the lens in the eye comprises releasing said suture means after seating a first portion of said position-fixation means in the eye and prior to a second portion of said position-fixation means reaching its final position within the eye.

11. a method according to claim 6 comprising the step of seating another portion of said position-fixation means in the posterior chamber of the eye, moving said one portion of the position-fixation means through the pupil also into the posterior chamber and thereafter releasing said suture means from its tightened into a loosened condition thereof.

* * * * *